United States Patent [19]

Flack et al.

[11] Patent Number: 5,385,936
[45] Date of Patent: Jan. 31, 1995

[54] GOSSYPOL ACETIC ACID FOR THE TREATMENT OF CANCER

[75] Inventors: Mary R. Flack, Kensington; Richard Knazek, Bethesda, both of Md.; Marcus Reidenberg, Scarsdale, N.Y.

[73] Assignee: The United States of America as represented by the Secretary of the Department of the Health and Human Services, Washington, D.C.

[21] Appl. No.: 551,353

[22] Filed: Jul. 12, 1990

[51] Int. Cl.$^6$ .................. A61K 31/225; A61K 31/19
[52] U.S. Cl. ................................. 514/548; 514/569
[58] Field of Search .......................... 514/569, 548

[56] References Cited

PUBLICATIONS

Kim et al., 1984, Contraception 312:5966–72.
Qian et al., 1984, Annual Review of Pharmcological Toxicology, vol. 24:329–60.
Rao et al., 1985, Cancer Chemother. Pharmacol., vol. 15, pp. 2–25.
Tanphaichitr et al., Biology of Reproduction, vol. 31, pp. 1049–1060, 1984.
Tso, Cancer Letters, vol. 24, pp. 257–261, 1984.
Wu et al., Cancer Research, vol. 49, pp. 3754–3758, Jul. 15, 1989.

*Primary Examiner*—Jerome D. Goldberg
*Attorney, Agent, or Firm*—Birch, Stewart, Kolasch & Birch

[57] ABSTRACT

A method for treating cancer in a human, which comprises administering to the human subject an anti-cancer effective amount gossypol acetic acid. Also included is a method for treating cancer in a human which comprises administering to the human subject an anti-cancer effective amount of gossypol acetic acid in combination with an anti-cancer effective amount of other conventional chemotherapeutic agents. Finally, the invention also encompasses a pharmaceutical composition comprising an anti-cancer effective amount of gossypol acetic acid, and an anti-cancer effective amount of a conventional chemotherapeutic agent, or combinations of the latter.

7 Claims, No Drawings

GOSSYPOL ACETIC ACID FOR THE TREATMENT OF CANCER

BACKGROUND OF THE INVENTION

1. Field of the Invention

The present invention is related to the use of gossypol acetic acid as an anti-tumor agent effective against human cancers susceptible thereto.

2. Description of the Related Art

Gossypol is a double biphenolic compound derived from crude cottonseed oil which has been shown to inhibit spermatogenesis, and which has been used extensively as a male contraceptive in China.

While gossypol has been shown to retard the growth of some cancers in nude mice, its effects vary widely from species to species (Qian, SZ (1984) *Ann. Rev. Pharmacol. Toxicol.* 24: 329–60; Kim et al. (1984) *Contraception* 312: 5966-72). The effect of gossypol on the mitochondrial accumulation of rhodamine has been shown to be lower in magnitude in human cells than in rat testicular tumor cells (Tanphaichitr et al. (1984) *Biol. of Reprod.* 31: 1049-1060). Furthermore, closely related compounds such as mitotane (ortho-para'-DDD), a biphenolic compound which has been used to treat adrenal cancer, are only of limited effectiveness in treating cancer in humans. In addition, the side effects produced at the doses required for response can be debilitating, and include anorexia, nausea, vomiting, and dizziness. Conventional chemotherapy such as with cytoxan, adriamycin, 5FU, and other agents has a low response rate, and side effects such as hair loss, bone marrow suppression, nausea, vomiting, and heart failure. Clearly, an alternate or adjuvant therapy with less toxic side effects is desirable.

The use of gossypol and related compounds as antitumor agents against cancers in humans has yet to be reported.

SUMMARY OF THE INVENTION

The present invention relates to the use of the acetic acid derivative of compounds with the following formula:

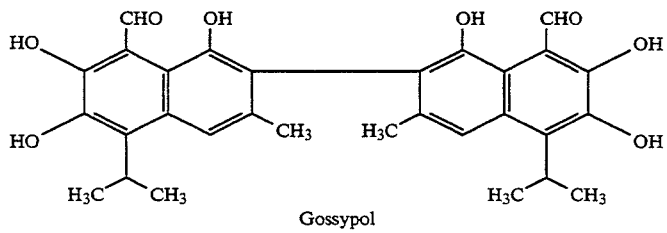

Gossypol in the treatment of human cancers susceptible thereto.

Pharmaceutical compositions useful in the present method of treatment include gossypol acetic acid, which contains both the positive and negative enantamers of gossypol, and formulations containing only one enantamer, as well as any physiologically acceptable salts, for either enteral or parenteral use. This compound may be used alone, or in combination with other conventional chemotherapeutic pharmaceutical compositions.

As compared to conventional therapies, the use of gossypol acetic acid to treat human cancers is associated with milder side effects. These include mild fatigue, muscle tremor, dry mouth, dry skin, and occasional nausea. These are well tolerated, and patients are able to continue their normal activities. In addition, conventional chemotherapeutic agents are associated with a high degree of drug resistance. As discussed below, anti-tumor gossypol acetic acid therapy has been demonstrated to be effective in patients who exhibit resistance to conventional anti-tumor agents.

As gossypol acetic acid is taken up into a number of human endocrine tissues, including the adrenal gland, testis, ovary, uterus, thyroid and pituitary, it can be used in the treatment of cancers of these organs, and against carcinoid tumors which are tumors of neuroendocrine tissue which may be located in the lung, pancreas, or gastrointestinal tract.

As previously noted, gossypol has been found to retard the growth of some cancers in nude mice. However, its effects vary widely from species to species. It could not be assumed, therefore, that the anti-cancer effects seen in animals would be seen in humans. A further unexpected feature associated with the use of gossypol acetic acid to treat cancer in human subjects as opposed to that in animals is that in the latter, higher doses of gossypol (e.g., 0.8 or 1.6 mg/mouse) have been shown to be lethal (Rao et al. (1985) *Cancer Chemother. Pharmacol.* 15: 20–25), negating any potential benefit of the drug in slowing cancer growth and prolonging survival. The present inventors have shown that the anti-tumor effect of gossypol acetic acid in humans occurs at doses which are approximately one tenth of those effective in animals, i.e., 1 mg/kg/d vs. 10 mg/kg/d. Toxicity in humans begins to occur at doses greater than 1-2 mg/kg/d. Therefore, the studies of gossypol in animals do not make the use of gossypol acetic acid for the treatment of cancer in humans, at appropriate doses, obvious in the latter.

Existing therapies for the treatment of human tumors, including adrenal, ovarian, thyroid, testicular, pituitary, prostate, and breast tumors, are multiple, including 5-fluorouracil, adriamycin, cytoxan, cisplatin, etoposide, suramin, and ortho-para'DDD (mitotane). These agents have a partial response rate of less than 20% for adrenocortical carcinoma, and less than 50% for other cancers. The toxicity of these agents, which is not exhibited by gossypol, includes myelosuppression, nausea, vomitting, anorexia, hair loss, cardiac failure and neurotoxicity. Thus, there is a need for anti-tumor agents with less toxicity which have activity against these tumors, and others, which are resistant to existing agents.

Gossypol acetic acid is a human anti-tumor agent which causes fewer side effects than such existing treatments.

Accordingly, it is an object of the present invention to provide a method for treating cancer in a human, which comprises administering to the subject an anti-cancer effective amount of gossypol acetic acid.

Another object of the present invention is to provide a method for treating cancer in a human which comprises administering to the subject an anti-cancer effective amount of gossypol acetic acid, and an anti-cancer effective amount of 5-fluorouracil, adriamycin, cytoxan, cisplatin, etoposide, suramin, mitotane, or other conventional chemotherapeutic agent, or combinations of these compounds.

A further object of the present invention is to provide a pharmaceutical composition comprising an anti-cancer effective amount of gossypol acetic acid and an anti-cancer effective amount of the compounds listed above, or combinations of these compounds.

Further scope of the applicability of the present invention will become apparent from the detailed description provided below. However, it should be understood that the detailed description and specific examples while indicating preferred embodiments of the invention, are given by way of illustration only since various changes and modifications within the spirit and scope of the invention will become apparent to those skilled in the art from this detailed description.

Detailed Description of the Invention

Reagents and Cells

Gossypol acetic acid was a gift from the National Research Institute for Family Planning (Beijing, China). The established line of small cell human adrenocortical carcinoma (SW-13) was purchased from the American Type Culture Collection (Rockville, Md.).

In Vivo Gossypol Acetic Acid Treatment

Nude Mice. Nude mice (Charles River, Kingston, N.Y.) weighing 20–35 g were caged in a temperature-controlled (26°–28° C.), 12 h/12 h light/dark animal room. A microporous cage bonnet served as an effective protective barrier between the animal and the outside environment. In addition, the room was continuously purged with High Efficiency Particle Attenuator-filtered air. The cages, feeders, and water bottles were designed to make standard mouse chow and water readily available while minimizing the opportunity for the transfer of communicable pathogens.

Transplantation of SW-13 Cells

Forty-nine adult male nude mice weighing 20–24 g were divided into two groups of 24 for control and 25 for gossypol acetic acid treatment. Gossypol acetic acid was suspended in 75% ethanol for 24h, then evaporated in vacuum chamber with desiccant, and finally suspended in sterilized 0.25% carboxymethylcellulose carrier. The gossypol acetic acid-treated group received 30 mg gossypol acetic acid/kg body weight/day via an orogastric tube. Control mice were fed an equal volume of carrier. Body weights were measured weekly. At the end of the first week of gossypol acetic acid treatment, $2 \times 10^6$ SW-13 cells were injected s.c. on the back of these mice, which continued to receive gossypol acetic acid or carrier for 5 additional weeks. Tumor surface areas (length $\times$ width, $cm^2$) were measured daily. After 5 weeks, the animals were decapitated.

Another experiment was designed wherein 48 adult male nude mice weighing 25–35 g were injected s.c. with $2 \times 10^6$ SW-13 cells. One month later, the animals were divided into two groups of 24. There were 7 nude mice without visible tumors in each group. The gossypol acetic acid treated animals received 30 mg gossypol acetic acid/kg body weight/day whereas control animals were fed an equal volume of carrier. Body weights and tumors sizes (lengths $\times$ width, $cm^2$) were measured weekly. During the 12th week of treatment, 5 control animals died. Since it appeared unlikely that the remaining control animals would survive for another week, they were then sacrificed. Autopsies were performed on all animals including those that died during the study period. Internal organs were examined for the presence of gross tumor.

Statistical Analysis

Data are expressed as the mean±SD unless otherwise indicated. Statistical comparisons were made using an unpaired Student's t test.

Effect of Gossypol acetic acid on SW-13 Tumor Bearing Nude Mice

In this experiment, nude mice had been given s.c. injections of SW-13 adrenocortical carcinoma 1 month prior to initiation of the treatment with either gossypol acetic acid or carrier.

During the subsequent 12 weeks of treatment, there were 10 deaths in the control group: 4 had apparent ascites, were jaundiced, and had large intraperitoneal tumors; 2 suffered from hind leg paralysis due to a tumor metastatic to the spinal column; 2 animals had small tumors, but both showed significant weight loss; 2 had demonstrated neither visible tumors nor an obvious cause of death. In contrast, only two deaths were observed in the gossypol acetic acid-treated group, one of them having ascites while the other had no apparent tumor at autopsy. Each treated mouse in the group received a total dose of 81.9 mg gossypol during the 12-week period.

As in the previous study, 12 weeks of gossypol acetic acid treatment had no signficant effect on body weights. At the end of the study period, the body weights in both groups were 32.2±3.8 and 30.9±3.6 g for the control and gossypol acetic acid-treated groups, respectively. After 12 weeks of treatment, the tumor prevalence had risen from 71 to 83% in the control group, while the gossypol acetic acid-treated group exhibited a decrease in tumor prevalence from 71% to 54%. This was accompanied by the death of 41.6% of the controls and 8.3% of the gossypol acetic acid-treated group (Table 1).

TABLE 1

Effect of gossypol acetic acid on tumor prevalence and mortality in mice having preexisting tumors

| | Control (%) | | Gossypol acetic acid (%) | |
|---|---|---|---|---|
| Week | Prevalence of tumor | Total deaths | Prevalence of tumor | Total deaths |
| 0 | 71 | 0 | 72 | 0 |
| 1 | 75 | 0 | 63 | 0 |
| 2 | 83 | 0 | 50 | 0 |
| 3 | 83 | 0 | 54 | 0 |
| 4 | 83 | 0 | 50 | 0 |
| 5 | 83 | 0 | 58 | 0 |
| 6 | 83 | 0 | 58 | 0 |
| 7 | 83 | 8.3 | 58 | 0 |
| 8 | 83 | 8.3 | 58 | 0 |
| 9 | 83 | 12.5 | 54 | 0 |
| 10 | 83 | 16.7 | 54 | 0 |
| 11 | 83 | 20.8 | 54 | 0 |
| 12 | 83 | 41.6 | 54 | 8.3 |

The mean tumor sizes of the control and the gossypol acetic acid treated groups were shown as a function of duration of treatment in Table 2. The slight decline in the mean tumor size observed towards the end of the study period was due to the fact that the majority of the control mice that died during the study had large tumors.

TABLE 2

Effect of gossypol acetic acid on mean tumor size

| Week | Mean tumor size (cm²) (mean ± SE) Control | Gossypol acetic acid |
|---|---|---|
| 0 | 0.09 ± 0.02 | 0.08 ± 0.02 |
| 1 | 0.22 ± 0.05 | 0.07 ± 0.02 |
| 2 | 0.28 ± 0.06 | 0.11 ± 0.04$^a$ |
| 3 | 0.35 ± 0.07 | 0.15 ± 0.05$^a$ |
| 4 | 0.59 ± 0.11 | 0.20 ± 0.07$^a$ |
| 5 | 0.66 ± 0.17 | 0.28 ± 0.08$^a$ |
| 6 | 0.87 ± 0.22 | 0.32 ± 0.10$^a$ |
| 7 | 0.97 ± 0.25 (n = 23) | 0.38 ± 0.12$^a$ |
| 8 | 1.16 ± 0.33 (n = 22) | 0.45 ± 0.14$^a$ |
| 9 | 1.07 ± 0.34 (n = 20) | 0.50 ± 0.15$^a$ |
| 10 | 1.14 ± 0.36 (n = 20) | 0.59 ± 0.18$^a$ |
| 11 | 1.39 ± 0.41 (n = 19) | 0.68 ± 0.21$^a$ |
| 12 | 0.96 ± 0.21 (n = 15) | 0.81 ± 0.25 (n = 22) |

$^a$P <0.05, control compared to gossypol acetic acid treated group; n = 24 unless otherwise indicated.

The total tumor burden of the two groups rose during the treatment period, the controls reaching a value twice that of the gossypol acetic acid group at the 12th week (FIG. 2).

Treatment of Human Metastatic Adrenal Cancer

Previous medical therapy for metastatic adrenocortical carcinoma has been largely unsuccessful. Based on the growth inhibitory effect of gossypol acetic acid on SW-13 human adrenocortical tumors in vivo in nude mice, discussed above, the effect of oral gossypol acetic acid treatment on metastatic adrenal cancer in a human patient was investigated.

A 36 year old man presented with a left sided adrenocortical carcinoma, 26×13 cm, invading the kidney and inferior vena cava. Surgical excision of all visible tumor was performed, and the patient was started on mitotane postoperatively. Pulmonary metastases were found six months later, which were resected. Six month following thoracotomy, multiple hepatic metastases were found. His tumor progressed despite treatment with Suramin and adriamycin/VP16.

At the time of gossypol acetic acid treatment, the patient had nocturnal dyspnea requiring supplemental oxygen therapy, markedly decreased exercise tolerance, persistent abdominal pain, and pedal edema. Physical examination revealed a cushingoid man with a blood pressure of 150/90, bilateral tender gynecomastia, a liver span of 14 cm, abdominal distention and fluid wave, and bilateral pitting edema to the knee.

Gossypol acetic acid, 10 mg compressed tablet, was given orally at a dose of 20 mg/d which was increased by 10 mg/d every three days to a dose of 50 mg/d.

During gossypol acetic acid treatment, the patient experienced fatigue, xerostomia, tremor, and transaminitis. After three weeks of gossypol treatment, CT scans showed complete resolution of pulmonary metastases and greather than 50% decrease in the size of the hepatic metastases, and an improvement in abdominal pain, ascites, and pulmonary function.

A summary of the results obtained in this and other human subjects during a phase I clinical trial of oral gossypol acetic acid for the treament of metastatic adrenocortical carcinoma is presented in Table 3.

TABLE 3

Summary of Preliminary Results of Phase 1 Clinical Trial of Oral Gossypol acetic acid for Adrenocortical Cancer

| Age/Sex | Site | Dose | Duration | Level | Side Effects | Response |
|---|---|---|---|---|---|---|
| 36/M* | Lung Liver | 40–60 mg/d | 28 weeks | 463 ng/dl | Xerostomia Fatigue Gynecomastia Transaminitis | Partial Response |
| 26/M | Lung Liver | 70 | 3 weeks | 1,025 | Xerostomia Nausea Transaminitis | Progression |
| 52/F | Abdomen | 40 | 6 weeks | 444 | Xerostomia Fatigue Nausea | Partial Response |
| 34/M | Abdomen Liver | 40–50 | 12 weeks | 291 | Xerostomia Fatigue Nausea | Stabilization |
| 27/M | Abdomen Pelvis | 50 | 6 weeks | 229 | Xerostomia Fatigue | Progression |

(*Patient descibed above)

Of these five patients, two exhibited partial tumor responses, one has stable disease, and two showed tumor progression.

Pharmaceutical Compositions and Modes of Administration of Gossypol Acetic Acid and Related Compounds The method of the present invention includes the administration of gossypol acetic acid, alone or in combination other conventional chemotherapeutic agents, and a pharmaceutically acceptable excipient, to a human subject.

In the methods according to the present invention pharmaceutical compositions containing gossypol acetic acid are administered in an effective amount to a human host for the treatment of a variety of human cancers including adrenal cancers and other cancers susceptible thereof.

In administering gossypol acetic acid for the treatment of cancer by the methods of the present invention, certain pharmaceutical compositions, doses, routes of administration, and desired blood levels may be employed. These are summarized in the table below. In each case, the indicated dose and blood level are approximate, e.g., for oral administration of gossypol acetic acid(+)-compressed tablet, the dose may be from about 40 to about 100 mg/d, and the desired blood level may be from about 400 to about 800 ng/dl.

TABLE 4

Pharmaceutical Formulations, Doses, Routes of Adminstration, and Effective Blood Levels of Gossypol Acetic Acid for the Treatment of Human Cancer.

| Formulation | Route | Dose | Blood Level |
|---|---|---|---|
| Gossypol acetic acid (+)-compressed tablet | Oral | 40–100 mg/d | 400–800 ng/dl |
| Gossypol acetic acid | Rectal, | 40–140 mg/d | 400–1000 ng/dl |

TABLE 4-continued

Pharmaceutical Formulations, Doses, Routes of Adminstration, and Effective Blood Levels of Gossypol Acetic Acid for the Treatment of Human Cancer.

| Formulation | Route | Dose | Blood Level |
|---|---|---|---|
| (+)-suppositories | vaginal | | |
| Gossypol acetic acid (±)-compressed tablet | Oral | 40–100 mg/d | 400–800 ng/dl |
| Gossypol acetic acid (±)-suppositories | Rectal, vaginal | 40–140 mg/d | 400–1000 ng/dl |

When administered orally, the drug may be taken in divided doses, two to three times a day.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for treating cancer in a human, wherein said cancer is susceptible to treatment with gossypol acetic acid, or physiologically acceptable salts thereof, which comprises administering to said human an anti-cancer effective amount of a compound selected from the group consisting of gossypol acetic acid, and physiologically acceptable salts thereof, and a pharmaceutically acceptable carrier.

2. The method of claim 1, wherein said cancer is adrenal, ovarian, thyroid, testicular, pituitary, prostate, or breast cancer.

3. The method of claim 2, wherein said cancer is adrenal cancer.

4. The method of claim 3, wherein said gossypol acetic acid is administered in a dose of from about 40 to about 100 mg/d.

5. The method of claim 3, wherein said gossypol acetic acid is administered in compressed tablet form containing 10 mg at an initial dose of 20 mg/d, which is then increased by 10 mg/d every three days to a final dose of 50 mg/d.

6. The method of claim 4, wherein said gossypol acetic acid is administered orally, in divided doses, two to three times a day.

7. The method of claim 5, wherein said gossypol acetic acid is administered orally, in divided doses, two to three times a day.

* * * * *